US00PP34902P2

(12) United States Plant Patent
Grauke et al.

(10) Patent No.: US PP34,902 P2
(45) Date of Patent: Jan. 10, 2023

(54) PECAN TREE NAMED 'SENECA'

(50) Latin Name: *Carya illinoinensis*
Varietal Denomination: 'Seneca'

(71) Applicant: The United States of America, as represented by the Secretary of Agriculture, Washington, DC (US)

(72) Inventors: Larry J. Grauke, College Station, TX (US); Tommy E. Thompson, College Station, TX (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 17/667,906

(22) Filed: Feb. 9, 2022

(51) Int. Cl.
*A01H 5/08* (2018.01)
*A01H 6/00* (2018.01)

(52) U.S. Cl.
USPC ..... Plt./153
CPC ..... *A01H 6/00* (2018.05)

(58) Field of Classification Search
USPC ..... Plt./153
CPC ..... A01H 5/0825
See application file for complete search history.

*Primary Examiner* — Kent L Bell
(74) *Attorney, Agent, or Firm* — John Fado; Ariel Atkinson

(57) ABSTRACT

A new and distinct variety of pecan tree, denominated 'Seneca', having a compact tree shape that is late to break bud in the spring, ceases growth early in the autumn, a determinate pattern of growth that is freeze tolerant, early season production of high-quality nuts, cream-colored kernels, and pecan scab fungus (*Venturia effusa*) disease resistance.

6 Drawing Sheets

Latin name of the genus and species of the plant claimed: 'Seneca' is a pecan tree that is a *Carya illinoinensis.*

Variety denomination: The new pecan tree is of the variety denominated 'Seneca'.

BACKGROUND OF THE NEW PLANT

'Seneca', tested as 1997-34-0017, is a 1997 progeny of a cross between two pecan varieties of northern origin, 'NC-2B' (seed parent) and 'NC-4' (pollen parent) (both unpatented), in Burleson County, Tex. 'NC-2B' and 'NC-4' are seedling selections obtained from Ontario, Canada. Genomic tests indicate 'NC-4' is a cross between 'Colby' (unpatented), an Illinois native pecan, and 'Peruque' (unpatented), a native pecan from Missouri. 'NC-2B' is a 'Colby' seedling. 'Seneca' was grown in Somerville, Tex. and was selected for further testing for its regular, early season production of high-quality nuts from compact, sturdy, disease-resistant trees suitable for northern pecan growing regions. 'Seneca' has been evaluated most extensively in orchards in Brownwood, Tex. in a test that comprised 49 selections with 3 control varieties ('Wichita', 'Pawnee', and 'Kanza') (all unpatented). All trees in this block had between 5 to 6 replicate grafted clones.

SUMMARY OF THE INVENTION

'Seneca' is distinguished from other pecan varieties due to the following unique combination of characteristics: a compact, sturdy tree that is late to break bud in the spring, ceases growth early in the autumn, a determinate pattern of growth that is freeze tolerant, early season production of high-quality nuts, cream-colored kernels, and pecan scab fungus (*Venturia effusa*) disease resistance. However, 'Seneca' has only been monitored in Central Texas and has not been observed under all environmental conditions and cultural practices. Therefore, some characteristics may differ outside of Central Texas or with different management practices.

BRIEF DESCRIPTION OF THE FIGURES

The accompanying drawings include color photographs that are as nearly true as it is reasonably possible to make in a color illustration of this type.

Figure 1:
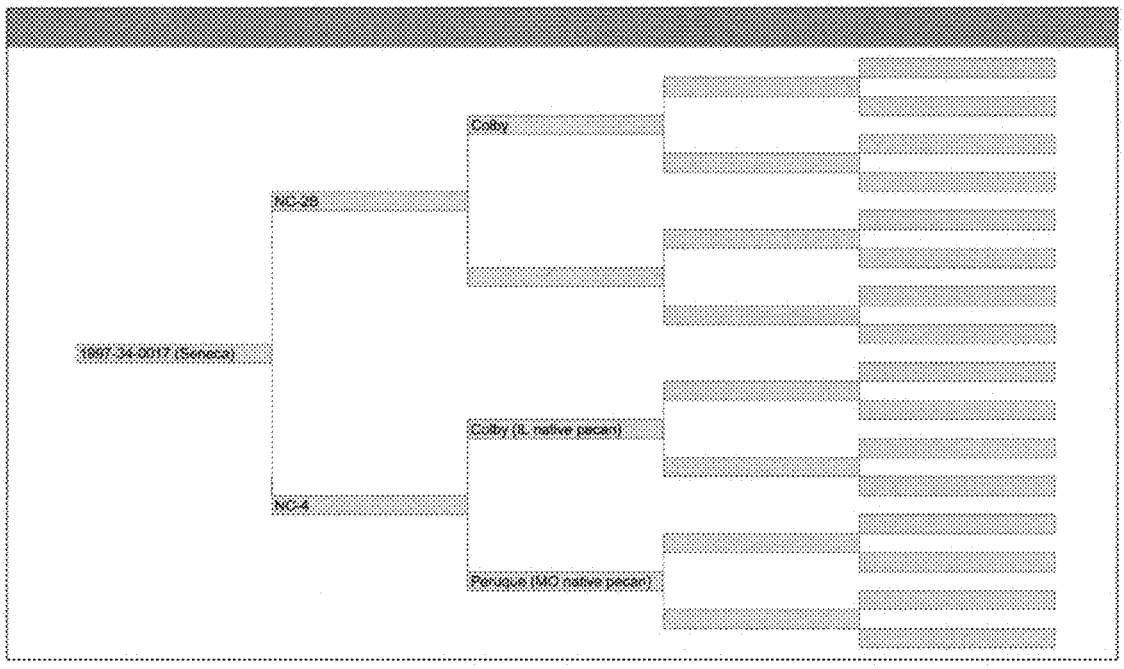
FIG. 1 is a chart showing the pedigree of 'Seneca'. Upper branch depicts the known ancestry of the seed parent ('NC-2B'). The lower branch depicts the known ancestry of the pollen parent ('NC-4').
Figure 2:
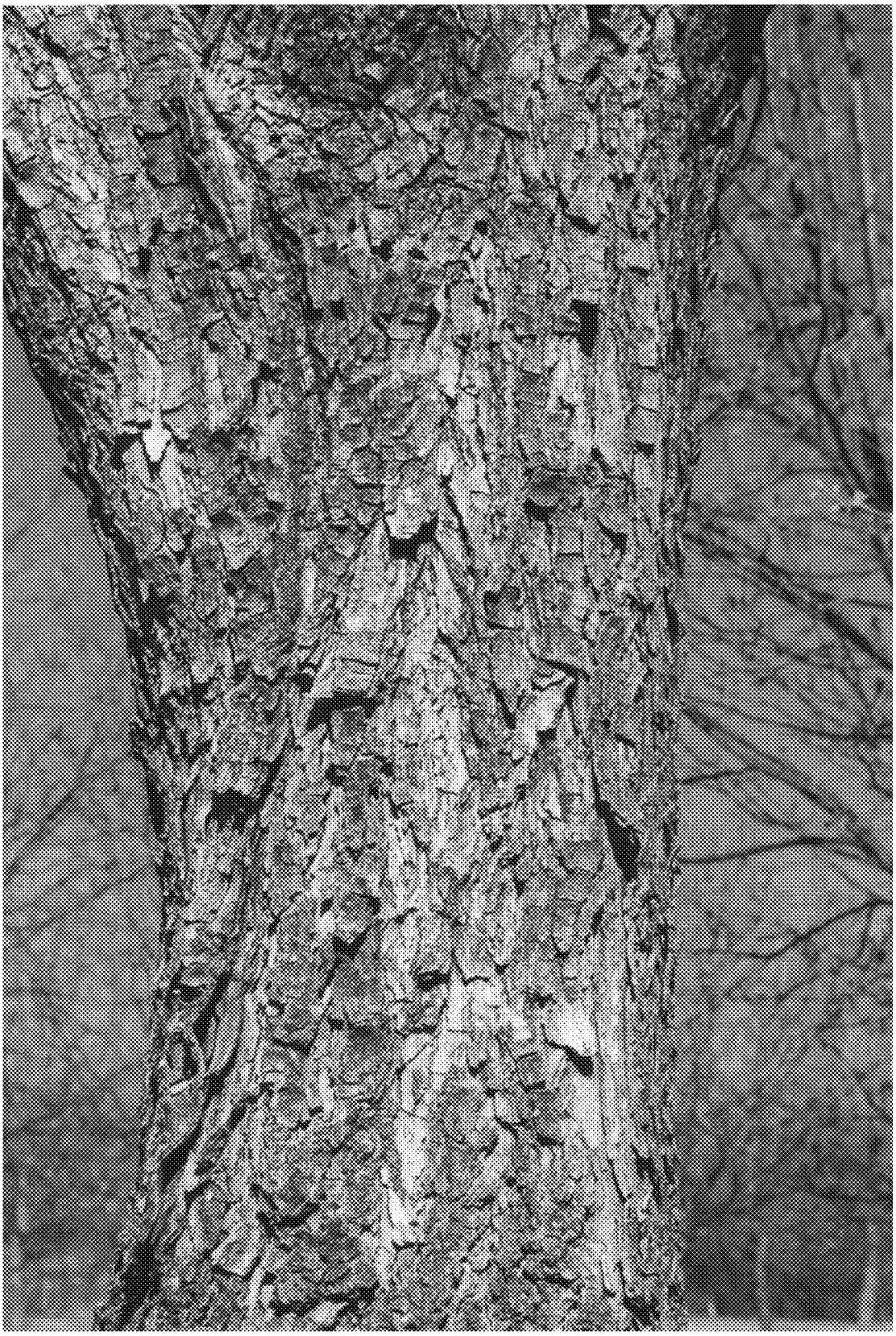
FIG. 2 is a photograph showing the bark texture of 'Seneca' at 15 years after grafting. Photo taken in Brownwood, Tex. on Apr. 7, 2021.

Due to photographical light, chemical development, processing and printing, the leaves and fruit depicted in these photographs may or may not be accurate when compared to the actual botanical specimen.

DETAILED BOTANICAL DESCRIPTION

All color descriptions are based on of the Munsell Plant Tissue Color Book: 2012 Year Revision (2019 Printing).

The botanical description below is based on five grafted clones of 'Seneca' located in the same orchard in Brownwood, Tex. In addition, the ortet for 'Seneca' is grafted into the canopy of one tree in Burleson County, Tex. Unless otherwise noted, the observations below were collected from April-June in 2021 (15 years after grafting).

Parentage:

*Seed parent*.—'NC-2B'.

*Pollen parent*.—'NC-4'.

Tree:

a. *Overall shape*.—General shape and height to width ratio: average 1.11. Tree shape is compact, with a slightly narrow canopy.

b. *Vigor*.—Vigorous. 'Seneca' was fruiting 3 years after grafting.

c. *Height*.—Average Height: 10.65 m.

d. *Width/trunk diameter*.—i. Canopy Width: 9.7 m. ii. Trunk Diameter: 286 mm.

e. *Trunk bark texture*.—Scaly when Mature.

f. *Trunk bark color*.—Grey-Brown — 2.5Y 5/2.

g. *Branch color*.—i. Woody stage branch shoots: Grey-Brown — 2.5Y 5/2. ii. Lenticels: Lenticel shape is highly variable. An average length would be 1.36 mm. The average width would be 1.06 mm. iii. Lenticel Color: Light Brown — 7.5YR 5/8.

h. *Internodes*.—The average length between the $3^{rd}$ and $4^{th}$ leaf from the base of the shoot is 14.67 mm.

i. *Disease and insect resistance*.—i. Pecan Scab, *Venturia effusa* (leaf and nut), data from 2010-2012, 2015, and 2016. In our unsprayed orchards, 'Seneca' has had only trace amounts of either leaf or nut scab.

j. *Leaves* (*data from June* 2020).—i. Leaf Arrangement and Color. 1. Leaves are odd-pinnately compound opposite. 2. Upper leaf color is Dark Forest Green — 7.5GY 3/4. 3. Lower leaf color is Green — 7.5GY 5/4. ii. The number of leaves per shoot and the number of leaflets per mature leaf. 1. Leaves per shoot: 5-10, Average 8. 2. Leaflets per leaf: 11-20, Average 16. iii. The angle of leaflet pairs to the rachis: 45°. iv. Leaflet blade: flat and not convoluted. v. Length and width of a mature leaf ($4^{th}$ leaf from the base of the shoot). 1. Length Range: 430-560 mm. Average: 495 mm. 2. Width Range: 275-385 mm. Average: 321 mm. vi. Petiole shape and color. Petiole shape is circular. Petiole color is Green-Yellow — 5GY 5/6. vii. Petiole length of the $4^{th}$ leaf from the base. 1. Length Range: 35.3-66.6 mm. Average: 53.1 mm. 2. Width Range: 2.3-3.33 mm. Average: 2.73 mm. viii. Leaflet size and shape ($4^{th}$ leaflet on $4^{th}$ leaf). 1. Leaflet Size Range: 110-180 mm. Average: 146.5 mm. 2. Width Size Range: 31-48 mm. Average: 37.7 mm. 3. Leaflet shape is falcate with serrate margins, an oblique base, and an acuminate tip. ix. Texture of upper leaf. The leaf texture is smooth on both the upper and lower surfaces with a glossy sheen. x. Sheen: glossy. xi. Petiolule. 1. Petiolule Length Range: 1.74-9.2 mm. Average: 5.32 mm. 2. Petiolule Width Range: 0.8-2.07 mm. Average: 1.27 mm. xii. Margin: Leaf margin is serrate. xiii. Tip Shape: Leaf tip is acuminate. xiv. Pubescence (Upper leaf and Lower leaf). Leaf pubescence is mostly glabrous with occasional pilose regions.

Inflorescence:

a. *General description*.—'Seneca' is monoecious, anemophilous, and protandrous (Table 1).

b. *Flowers*.—i. The number of pistillate flowers and arrangement of the flowers. 4-7 individual pistillate flowers per pedicel spike are borne alternately on terminally positioned spikes. ii. Description of the pistillate flower and pedicels. Mid-to-late pistil receptivity with red stigmas. iii. Staminate catkin length and width (in mm). 1. Catkin Length Range: 62-133 mm. Average: 97.6 mm. 2. Catkin Width Range: 5-8 mm. Average: 6.5 mm. iv. Staminate color, pollen color. 1. Staminate color: Golden — 2.5GY 6/10. 2. Pollen color: Yellow — 5Y 8/10. v. Involucre size, including the stigma (length and width). 1. Involucre Length Range: 6.58-10.67 mm. Involucre Length Average: 8.42 mm. 2. Involucre Width Range: 1.59-2.22 mm. Involucre Width Average: 1.97 mm. vi. Description of Anthocyan on stigma. The stigmas are red sometimes containing patches of green. vii. Flower pistil color(s). Dominant stigma color is red (5R 3/2) with occasional splashes of green (5GY 5/6). viii. Number and color of bracts, shape (lanceolate), flower length and width, and description of petal fusion and the end resulting flower shape (copular involucre): Three lanceolate bracteoles are present and one bract (all green: 5G 4/8). The bracteoles and bract are fused at the base to form a copular involucre.

Fruit:

a. *Mature fruit*.—Is dehiscent.

b. *Shuck*.—i. Shuck color is green — 5GY 7/10.

c. *Fruit split during water stage*.—Has not been observed to be a problem.

d. *Shuck decline during kernel formation*.—Has not been observed to be a problem.

Nuts:

a. *Observations are from detailed measurements of five nuts per year from multiple years*.—2009-2018 (except no data in 2013).

b. *Size*.—i. The average nut length is about 37.7 mm. The average nut width is about 20.9 mm. The length-to-width ratio is 1.80. ii. Nut cross-section is round with a flatness ratio (width across sutures to the width between sutures) of 1.06.

c. *Form*.—i. The shape of the nut with the shape of the cross-section. The nut is elliptic shaped (length to height ratio 1.73) with a round cross section. ii. Base shape: Oblique. iii. Apex shape: Acute. iv. Presence and locations of defining features: Nut apex is sometimes grooved. v. Description of shell suture: Often, but not always, elevated. vi. Description of shell surface: Black lines and patches stretch from the apex to the midpoint of the nut, covering up to 50% of the upper nut surface. The lower 10-50% of the nut may be covered with black speckles. vii. Description of shell topography: Smooth.

d. *Dorsal grooves*.—Kernels have deep, but wide dorsal grooves that do not trap packing material.

e. *Ventral grooves*.—Kernels have a pronounced ventral groove that does not trap packing material.

f. *Weight*.—7.36 g (data from 2009-2018, without 2013).

g. *Cluster size*.—On average 2.62 nuts per cluster (data from 2009-2012, 2014, 2016, and 2017).

h. *Shell topography*.—Generally smooth, with a slight ridge on the suture.

i. *Shell thickness*.—1.22 mm average, moderately thick.

j. *Shell color*.—Brown — 7.5YR 4/4.

k. *Kernel color*.—Cream color: 10YR 7/4.

l. *Kernel percentage*.—57.8% Average.

m. *Nut maturity date*.—September 23rd.

COMPARISON TO OTHER VARIETIES

Figure 3:
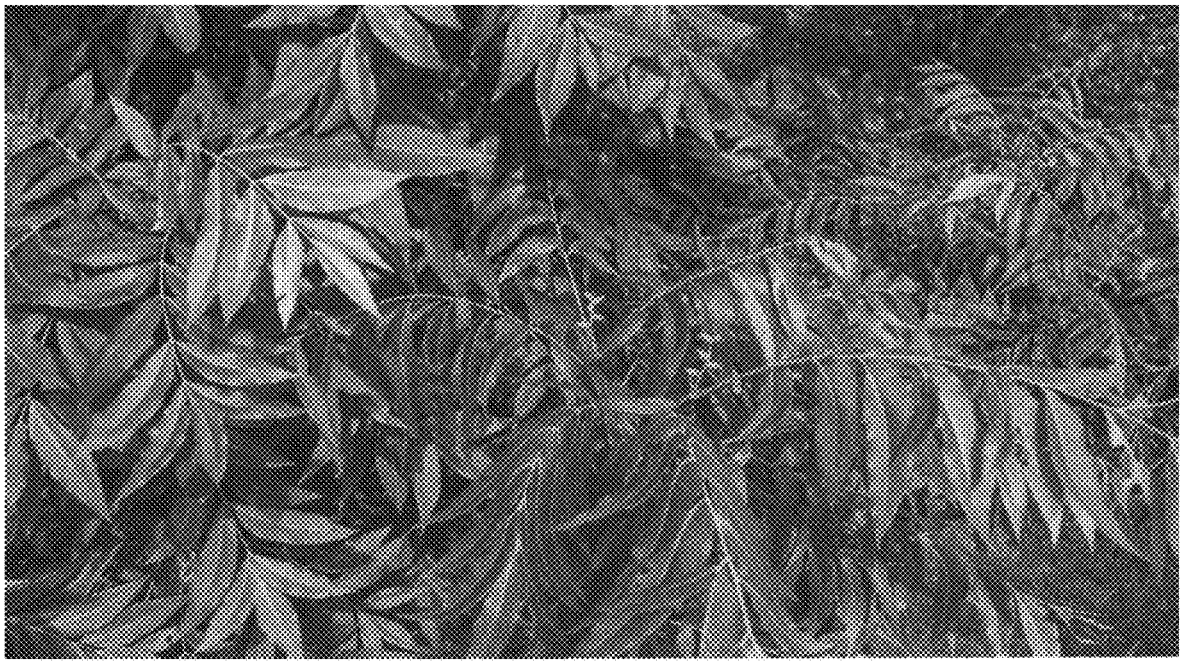
FIG. 3 is a photograph of the leaf architecture of 'Seneca' at 15 years after grafting. Photo taken in Brownwood, Tex. on Jun. 4, 2021.
Figure 4:
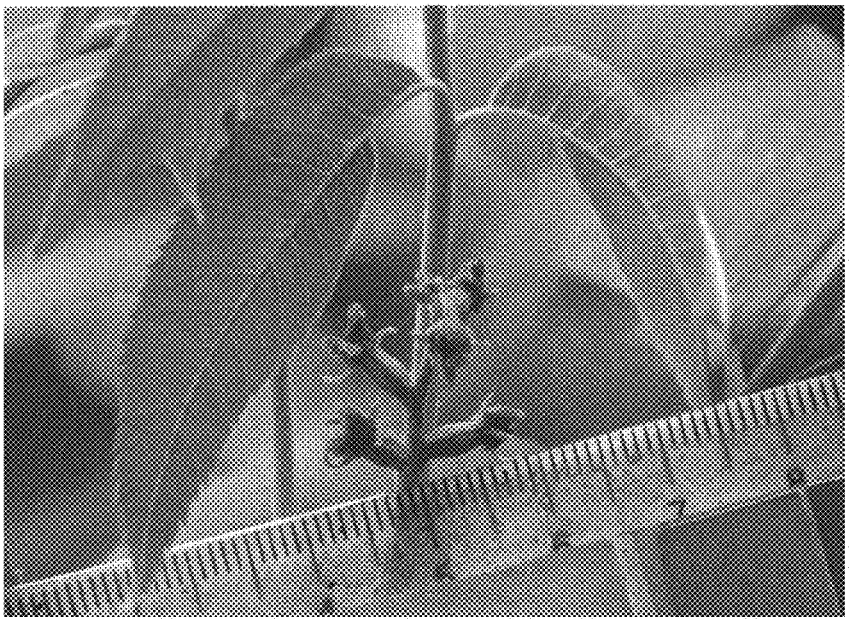
FIG. 4 is a photograph of a red 'Seneca' pistillate flower. Photo taken in Brownwood, Tex. on May 13, 2021.

'Seneca' is a new pecan cultivar that produces high-quality pecans with attractive, cream kernels on compact disease-resistant trees suitable for the northern growing region. 'Seneca' has dark forest green leaves comparable to 'Pawnee'. Leaflet orientation is similar to most pecan trees, wherein the opposite leaflet pairs are oriented about 45 degrees from the rachis (FIG. 3).

'Seneca' is protandrous. It has mid-to-late season pollen shed, comparable to 'Wichita', and mid-to-late season pistillate receptivity, comparable to 'Pawnee' in Brown County, Tex. (Table 1). It usually bears 4-7 alternately-positioned pistillate flowers per pedicel spike. 'Seneca' has pistillate flowers with reflexed, red stigmas. It should be a good pollinizer for and be well pollinized by 'Kanza' and 'Lakota' (unpatented) . On average, spring bud break for 'Seneca' was in early April in Brown County, Tex. (91.1 Julian days), around the same time as 'Pawnee' (92.3 Julian days) and 'Kanza' (89.6 Julian days) and about a week later than 'Wichita' (81.8 Julian days) (Table 2). No damage was observed from the prolonged freeze in early February 2021 in Central Texas. 'Seneca' exhibited minimal leaf scab fungus (*Venturia effusa*) susceptibility within our unsprayed orchards in Brownwood, Tex. Its pollen parent 'NC-4' showed minimal leaf scab susceptibility and some nut scab susceptibility in a separate orchard in Burleson County, Tex. Within our Brownwood orchard from the years 2010-2012 and 2015, 'Pawnee' showed a surprising lack of leaf and nut scab infection, despite nearby 'Wichita' trees showing some infection. 'Seneca' also displayed minimal infection during those years. From 2015-2017, we observed the expected levels of nut scab infection for the known-susceptible varieties in that orchard while 'Seneca' continued to display resistance. The average nut scab observed that period for 'Seneca' was only 1.50 percent on the standard area diagram scale of 1 to 100 percent, comparable to 'Kanza' at 1.42 percent, with 'Pawnee' at 30.89 percent and 'Wichita' at 91.51 percent infection (Table 2); indicating a much greater resistance to scab fungus than susceptible control varieties. However, 'Seneca' is likely to require fungicide management in more humid environments.

Figure 5:
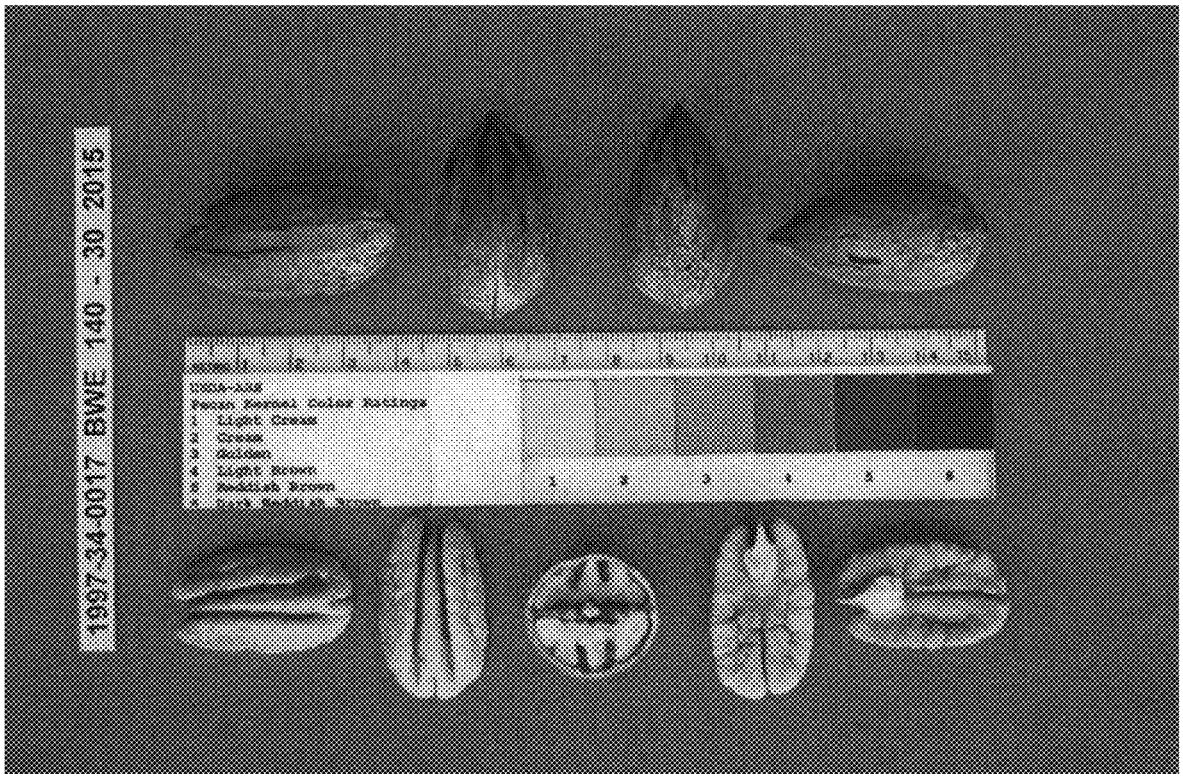
FIG. 5 is a photograph of a 'Seneca' nut quality panel. Photo taken in Brownwood, Tex. on Dec. 1, 2015.
Figure 6:
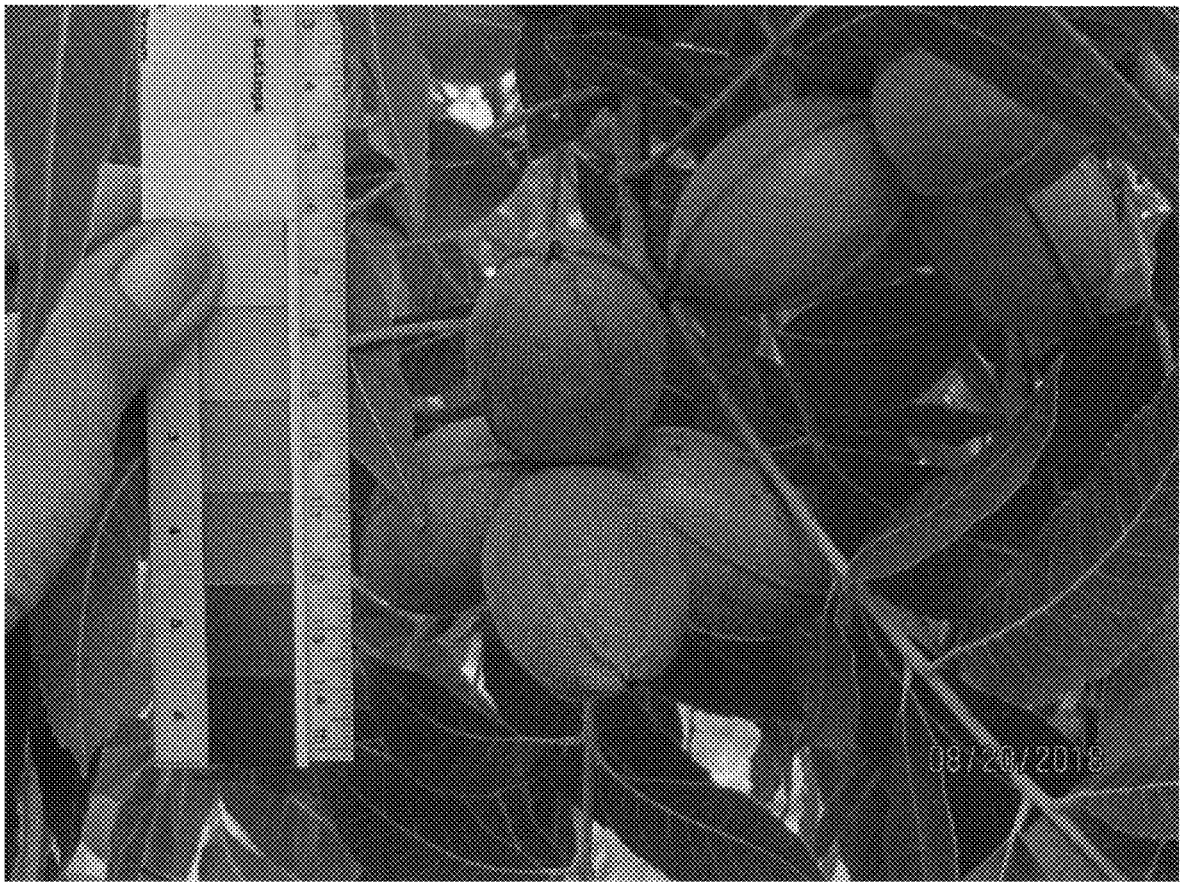
FIG. 6 is a photograph of 'Seneca' nut clusters. Photo taken in Brownwood, Tex. on Aug. 20, 2018.
Figure 7:
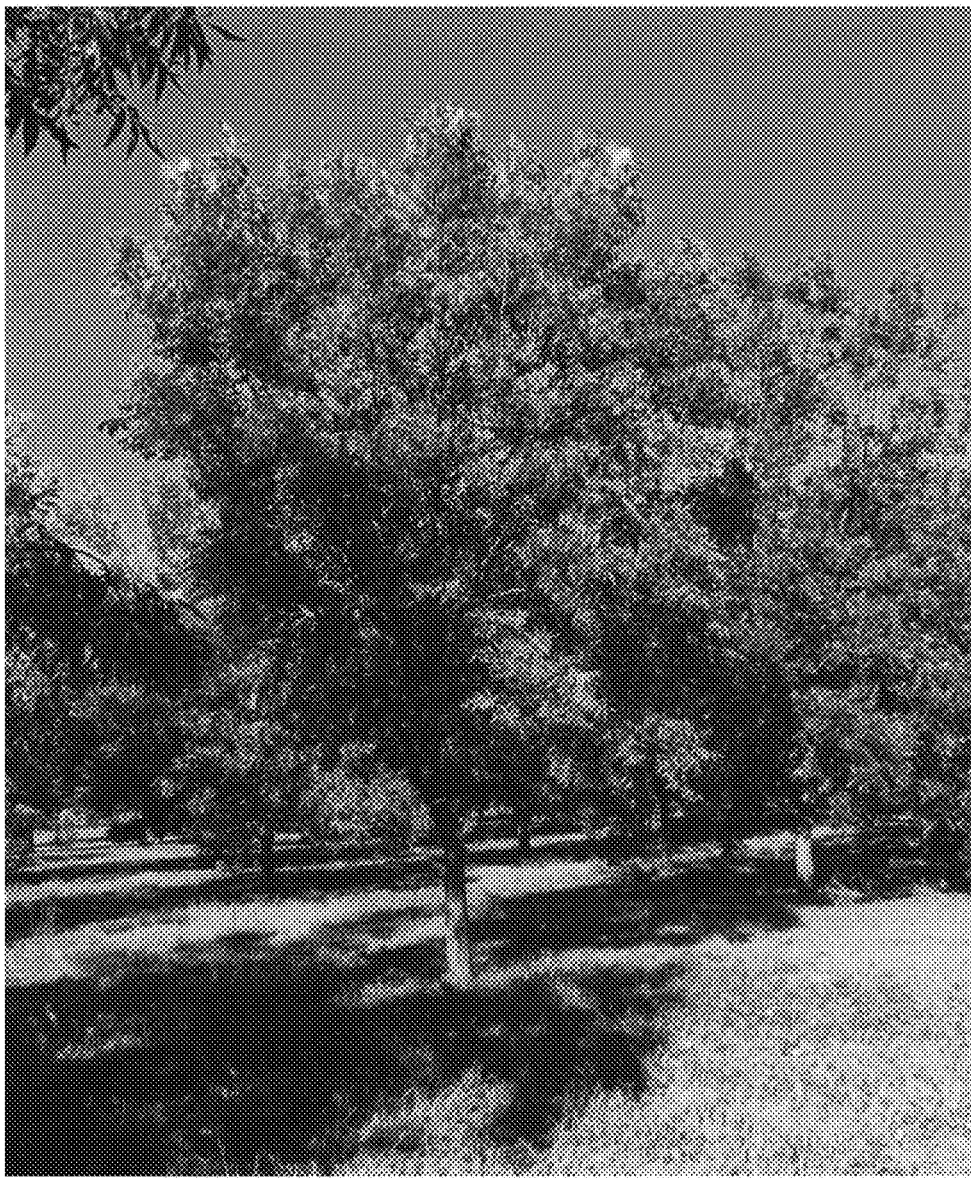
FIG. 7 is a photograph of the canopy structure of a 9-year-old 'Seneca' tree on an 'Apache' (unpatented) seedling rootstock. Photo taken in Brownwood, Tex. on Oct. 5, 2016.

'Seneca' produces high-quality nuts, even under limited irrigation, that mature early and are ready to harvest in late September in Central Texas at the same time as 'Pawnee'. On average, 'Seneca' nuts mature around September 23rd (265.5 Julian days) (Table 3). The average nut weight is 7.36 grams for 'Seneca', compared to 8.52 g for 'Pawnee' and 7.06 for 'Wichita'. The average number of nuts per pound is 62.92 for 'Seneca', compared to 54.63 for 'Pawnee' and 67.19 for 'Wichita'. The pollen parent, 'NC-4', produced an average of 63.85 nuts per pound in Burleson County, Tex. 'Seneca' has nut dimensions most comparable to 'Kanza' among the controls in this test. Nut percent kernel averages 57.38 with a cream color compared to 'Pawnee', which has an average 59.14 percent kernel with golden kernels, and 'Kanza' which has a 52.83 percent kernel with golden kernels in Brownwood, Tex. (FIG. 5). The pollen parent, 'NC-4', planted in Burleson County, Tex. has a 54.57 percent kernel with dark golden kernels. 'Seneca' averages 2.62 nuts per cluster, compared to 3.28 for 'Pawnee', 2.99 for 'Kanza', and 3.31 for 'Wichita' (Table 3). In the 6th leaf year (2012), 'Seneca' bore 12.05 dry weight pounds of nuts, compared to 21.16 for 'Pawnee' and 22.05 for 'Wichita' (Table 4).

Further detailed information is presented in the tables below:

TABLE 1

Bud break, pollen shedding and stigma receptivity of 'Seneca' and other 3 pecan cultivars (control) in the USDA-ARS National Pecan Advanced Clone Testing System (NPACTS) orchard in Brownwood, Texas.

| Cultivar | Dichogamy | Bud Break* | 5th Week April** | 1st Week May | 2nd Week May |
|---|---|---|---|---|---|
| Seneca | Protandrous (type I) | April 1st (91.1 days) AB | | PS | PS/PR |
| Kanza | Protogynous (type II) | March 31st (89.6 days) B | PR | PR | PS |
| Pawnee | Protandrous (type I) | April 2nd (92.3 days) A | PS | PS | PR |
| Wichita | Protogynous (type II) | March 23rd (81.8 days) C | PR | PR/PS | PS |

Note:

A total of 52 entries (49 breeding lines and 3 cultivars) (grafted onto a rootstock cultivar 'Apache' in 2007) were arranged in the NPACTS orchard with a randomized complete block design in 6 blocks in Brownwood, Texas.

*Bud break was rated using the following scale: 1 = dormant, 2 = swell, 3 = inner scale split, 4 = burst, 5 = first leaflet expansion, 6 = 25% expansion, 7 = to 50% leaf expansion, 8 = to 75% leaf expansion, 9 = fully expanded leaves. Data is the average of three years records (2016, 2017, and 2021). For comparison, Julian days (in bracket) were calculated when bud break scale reached to scale 3.

**PS = Pollen Shedding, PR = Pistillate Receptivity.

Values within column followed by a common letter are not significantly different according to Student's t test at $p < 0.05$.

TABLE 2

Comparison of average leaf and fruit scab susceptibility of 'Seneca' and three cultivars (controls) in the USDA-ARS National Pecan Advanced Clone Testing System (NPACTS) orchard (unsprayed) in Brownwood, Texas.

| Cultivar | Leaf Scab* | Nut Scab* | Nut Scab Percent** |
|---|---|---|---|
| Seneca | 1.00 B | 1.04 B | 1.50 C |
| Kanza | 1.00 B | 1.04 B | 1.42 C |
| Pawnee | 1.00 B | 1.42 B | 30.89 B |
| Wichita | 2.71 A | 3.49 A | 91.5 A |

*measured with Hunter-Roberts Scale, 1 = no scab, 5 = greater than 50% coverage of leaves or fruit with scab lesions. Data are four years' average (2010-2012 and 2015).

**measured with standard area diagram scale (% of nut with scab lesions) across three years (2015-2017).

Values within column followed by a common letter are not significantly different according to Student's t test at $p < 0.05$.

TABLE 3

Comparison of average nut characteristics of five nuts per tree for four cultivars in Brownwood, TX from 2009-2018 (Wt./nut [g], Nuts/lbs. [no.], Nut length [mm], Nut Length/width, Nut flatness [ratio of nut width across suture to between suture], Kernel [percentage], Nut Maturity Date [75% shuck dehiscence]. Nut sampling was incomplete in 2013.

| Cultivar | Nut Length mm | Nut Height mm | Nut Width mm | Nut Weight gm | Kernel Percent |
|---|---|---|---|---|---|
| Seneca | 37.74 B | 21.77 C | 20.93 C | 7.36 B | 57.38 B |
| Kanza | 34.58 C | 22.92 B | 21.71 AB | 6.61 C | 52.83 C |
| Pawnee | 41.06 A | 23.79 A | 21.43 B | 8.52 A | 59.14 A |
| Wichita | 41.23 A | 21.97 D | 21.97 A | 7.06 B | 55.58 B |

TABLE 3-continued

Comparison of average nut characteristics of five nuts per tree for four cultivars in Brownwood, TX from 2009-2018 (Wt./nut [g], Nuts/lbs. [no.], Nut length [mm], Nut Length/width, Nut flatness [ratio of nut width across suture to between suture], Kernel [percentage], Nut Maturity Date [75% shuck dehiscence]. Nut sampling was incomplete in 2013.

| Cultivar | Nuts Per Lb. | 75% Shuck Split (Julian Days) | Nut Height to Width Ratio |
|---|---|---|---|
| Seneca | 62.92 B | Sep 23rd (2653) C | 1.04 |
| Kanza | 69.48 A | Sep 28th (270.54) B | 1.06 |
| Pawnee | 54.63 C | Sep 24th (267.01) C | 1.11 |
| Wichita | 67.19 A | Oct 20th (292.74) A | 0.96 |

Values within column followed by a common letter are not significantly different according to Student's t test at $p < 0.05$.

TABLE 4

Comparison of Dry Weight Nut Yield (average lbs./tree) of five to six replicates of four cultivars growing in one orchard in Brownwood, Texas from 2009-2012. Precocity (years to initial fruiting after nursery transplant) can also be interpreted from this data. These trees were grafted in 2007.

| Cultivar | Yr. 3 2009 | Yr. 4 2010 | Yr. 5 2011 | Yr. 6 2012 | ABI* |
|---|---|---|---|---|---|
| Seneca | — | 0.35 | 0.04 | 12.05 | 0.88 |
| Kanza | 0.07 | 0.75 | 0.44 | 8.26 | 0.66 |

TABLE 4-continued

Comparison of Dry Weight Nut Yield (average lbs./tree) of five to six replicates of four cultivars growing in one orchard in Brownwood, Texas from 2009-2012. Precocity (years to initial fruiting after nursery transplant) can also be interpreted from this data. These trees were grafted in 2007.

| Cultivar | Yr. 3 2009 | Yr. 4 2010 | Yr. 5 2011 | Yr. 6 2012 | ABI* |
|---|---|---|---|---|---|
| Pawnee | 0.18 | 0.46 | 0.18 | 21.16 | 0.62 |
| Wichita | 0.04 | 0.55 | 2.09 | 22.05 | 0.76 |

*The alternate bearing index (ABI) is a measure of a cultivar's tendency to produce alternating high and low yields. Ranges are from 0 to 1, with 0 = no alternation and 1 = complete alternation (Pearce and Dobersek-Urbanc, 1967).

$ABI = 1/(n-1) \times \{|(a2-a1)|/(a2+a1) + |/(a3-a2)|/(a3+2) \ldots + |(an)-a(n-1))|/(a(n) + a(n-1))\}$ where n = number of years, and a1, a2, . . . , a(n − 1 ), an = yield of corresponding years.

Values within column followed by a common letter are not significantly different according to Student's t test at $p < 0.05$.

TABLE 5

Comparison of Average Nut Cluster Size (Nuts/ Cluster [no.]) of five to six replicates of four cultivars at Brownwood, Texas from 2009-2017)

| Cultivar | Yr. 3 2009 | Yr. 4 2010 | Yr. 5 2011 | Yr. 6 2012 | Yr. 8 2014 | Yr. 10 2016 | Yr. 11 2017 | Average |
|---|---|---|---|---|---|---|---|---|
| Seneca | 2.50 | 2.00 | 1.60 | 3.69 | 2.28 | — | 2.76 | 2.62 B |
| Kanza | 1.47 | 2.56 | 2.33 | 3.23 | 2.93 | 4.02 | 3.02 | 2.99 A |
| Pawnee | — | 2.30 | 1.94 | 3.93 | 2.68 | 4.83 | 2.67 | 3.28 A |
| Wichita | 2.00 | 3.23 | 2.80 | 3.88 | 3.10 | 4.33 | 3.22 | 3.31 A |

Note:

No nuts were harvested in 2013 and 2015. Sampling was incomplete in 2016.

Values within column followed by a common letter are not significantly different according to Student's t test at $p < 0.05$.

We claim:

1. A new and distinct variety of pecan tree named 'Seneca' as illustrated and described herein.

* * * * *